(12) United States Patent
Garrison

(10) Patent No.: US 6,555,095 B1
(45) Date of Patent: Apr. 29, 2003

(54) TOPICAL COMPOSITIONS AND METHODS OF APPLICATION

(75) Inventor: Mark S. Garrison, Suffern, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 10/017,552

(22) Filed: Dec. 14, 2001

(51) Int. Cl.⁷ .............................. A61K 7/42; A61K 7/44; A61K 7/00
(52) U.S. Cl. ........................... 424/59; 424/60; 424/400; 424/401
(58) Field of Search ............................ 424/59, 60, 400, 424/401

(56) References Cited

U.S. PATENT DOCUMENTS

| | | |
|---|---|---|
| 4,015,009 A | 3/1977 | Chakrin et al. |
| 4,024,106 A | 5/1977 | Mader |
| 4,455,295 A | 6/1984 | Hopp et al. |
| 4,515,774 A | 5/1985 | Conner et al. |
| 4,562,067 A | 12/1985 | Hopp et al. |
| 4,613,499 A | 9/1986 | Conner |
| 4,710,373 A | 12/1987 | Nakamura et al. |
| 4,833,259 A | 5/1989 | Erlemann et al. |
| 4,837,010 A | 6/1989 | Hotta et al. |
| 4,863,963 A | 9/1989 | Nakai et al. |
| 5,049,685 A | 9/1991 | Saito |
| 5,093,366 A | 3/1992 | Nakai et al. |
| 5,160,731 A | 11/1992 | Sabatelli et al. |
| 5,191,113 A | 3/1993 | Nakai et al. |
| 5,204,462 A | 4/1993 | Kobayashi et al. |
| 5,338,539 A | 8/1994 | Raspanti |
| 5,426,210 A | 6/1995 | Kato et al. |
| 5,475,126 A | 12/1995 | Yoshida et al. |
| 5,783,173 A | 7/1998 | Bonda et al. |
| 5,788,964 A | 8/1998 | Baral et al. |
| 5,888,481 A | 3/1999 | Horn et al. |
| 5,917,088 A | 6/1999 | Philippe |

*Primary Examiner*—Shelley A Dodson
(74) *Attorney, Agent, or Firm*—Ohlandt, Greeley, Ruggiero & Perle, LLP

(57) ABSTRACT

There are topical emulsion compositions having a cosmetic drug or medicinal active, a novel compound of the present invention, and a vehicle. The novel compound is represented by a formula selected from the group consisting of L—A—H and A—L—H, wherein L is a lipophilic moiety, A is an aromatic moiety, and H is a hydrophilic moiety. Also provided are methods of emulsifying a composition; improving the photostability of a composition; and enhancing the effectiveness of a sunscreen composition.

63 Claims, No Drawings

TOPICAL COMPOSITIONS AND METHODS OF APPLICATION

BACKGROUND OF THE INVENTION

1. Field of the Invention

The present invention relates to topical compositions. More particularly, the present invention relates to compositions having a cosmetic, drug or medicinal active and a compound (hereinafter "novel compound") having an aromatic moiety, a lipophilic moiety, and a hydrophilic moiety in which the novel compound has emulsifying and/or photostabilizing properties.

2. Description of the Prior Art

Many cosmetic compositions are susceptible to photodegradation. Prior art methods of addressing such concerns have included packaging such compositions in special containers, such as containers formed from light-impervious materials. However, these types of containers are not always preferred in the consumer product industry where packaging can determine the success of the product. It would be desirable to have compositions, especially cosmetic and personal care compositions, that have improved photostability.

In addition, emulsions have one or more emulsifiers to maintain and stabilize phase separation and dispersion of the internal phase within the external phase. Emulsifiers also help prevent precipitation and/or crystallization of components, including sunscreen actives. Emulsifiers also improve the overall aesthetic appearance of the emulsions.

It would be desirable to have emulsions that provide a greater degree of phase separation and stability, reduced incidence of precipitation and/or crystallization of components, and improved overall aesthetic appearance. It is also desirable to formulate a product using the least amount of emulsifier possible, in order to maintain as low a cost as possible for the finished formulation. Furthermore, it is desirable to improve the photostability of topical compositions.

SUMMARY OF THE INVENTION

It is an object of the present invention to provide a topical composition that has improved photostability.

It is also an object of the present invention to provide an emulsion composition that provides a high degree of stability and a low incidence of phase separation, precipitation and/or crystallization of emulsion components.

It is also an object of the present invention to provide a composition that is suitable for topical application and is cosmetically elegant and has a pleasing aesthetic appearance.

It is another object of the present invention to improve the photostability of a topical composition having a cosmetic, drug or medicinal active, particularly one containing one or more sunscreen actives.

It is yet another object of the present invention to provide a novel compound that, when used in conjunction with a sunscreen, enhances the sunscreen protection factor ("SPF") provided by the composition.

These and other objects and advantages of the present invention are achieved by utilizing the topical compositions of the present invention. The compositions have a cosmetic, drug or medicinal active, preferably having an aromatic moiety, the novel compound of the present invention, and a vehicle. The novel compound in the compositions has a formula selected from the group consisting of L—A—H (Formula I) and A—L—H (Formula II), wherein L is a lipophilic moiety, A is an aromatic moiety having an ultraviolet absorption maximum between 290 and 400 nanometers, preferably when measured in ethanol, and H is a hydrophilic moiety.

It is another object of the present invention to provide a solubilizer to improve the solubility of a cosmetic or medicinal active in a topical composition.

It is another object of the present invention to improve the photostability of a composition, particularly one having a sunscreen active, by adding to it the novel compound.

It is another object of the present invention to improve the effectiveness of a sunscreen composition by adding to it the novel compound.

DETAILED DESCRIPTION OF THE INVENTION

The present invention relates to topical compositions having improved photostability and decreased photodegradation. The compositions may be emulsions, especially aqueous emulsions, and exhibit a high degree of stability and a low incidence of phase separation, precipitation and/or crystallization of ingredients. The compositions also have an excellent overall aesthetic appearance.

The novel compounds have a formula that is selected from the group consisting of L—A—H (Formula I) and A—L—H (Formula II) wherein A is an aromatic moiety, L is a lipophilic moiety, and H is a hydrophilic moiety. Novel compounds of the formula L—A—H are preferred. It is within the scope of the present invention that the novel compounds may have additional moieties, but the novel compounds must have at least the above three moieties (i.e., L, A and H) in either sequence indicated. Additional moieties may be attached to either end or between the moieties. Although Formula I novel compounds are preferred where ease of synthesis and cost are of concern, Formula II novel compounds are believed to better achieve the benefits of the present invention.

The lipophilic moiety may be a chain, preferably linear, having 2 to 24 carbon atoms. The chain may be branched or unbranched and saturated or unsaturated. The lipophilic moiety may also be a nonionic polyoxyalkylene chain of the formula $(C_xH_yO)_n$, where x is 3 or more, n is 2 or more, and y is from $2x-2$ to $2x$. The lipophilic moiety of the novel compound has an affinity for the oil phase of the emulsion.

Examples of suitable lipophilic moieties include branched or unbranched alkyl groups having from about 4 to about 24 carbon atoms, and preferably from about 8 to about 18 carbon atoms. Other examples include polyoxypropylene chains having a range of propoxylation, i.e. number of propylene oxide (PO) units, from 2 to about 160, preferably from about 5 to about 40 and most preferably from about 10 to about 20. As is known by those skilled in the art, the degree of propoxylation may be adjusted to provide desired properties.

The aromatic moiety has at least one benzene ring, which may be functionalized or nonfunctionalized. The aromatic moiety has an intrinsic ultraviolet absorption maximum between 290 and 400 nanometers that imparts to the novel compound an absorptivity value of about 5 or more. The absorptivity value is measured as defined in US Pharmacopiea 25, which is incorporated herein by reference, especially page 2075 thereof. It is known and understood in the art that a compound may have more than one UV maximum, since the maximum absorbance peaks are due to electronic transitions, and often more than one such transition is observed. The aromatic moiety may have para, meta, or ortho substitution. Para substitution is most preferred followed by meta substitution. In addition, when the novel compound is the structure represented in Formula I, it is preferred that the lipophilic and hydrophilic moieties are in the para positions. The aromatic moiety and the lipophilic moiety of the novel compound are different. The lipophilic moiety preferably does not have an aromatic group therein.

Examples of suitable aromatic moieties useful in the present invention include, but are not limited to, one or more salicylates, anthranilates, cinnamates, methoxycinnamates, ferulates, para amino benzoates, dibenzoyl methanes, benzophenones, phenyl benzamidazoles, cyano diphenyl acrylates, benzylidenes, hydroxy benzylidenes, biphenyls, terephthalylidenes, triazines, naphthalene dicarboxylates, digallic acids, gallic acids, gallates, triazones, or any combinations thereof. Preferred aromatic moieties are cinnamates, benzophenones, dibenzoyl methanes, and salicylates. A preferred dibenzoyl methane moiety is butylmethoxydibenzoyl methane. By way of example, the methoxycinnamate moiety is depicted in Formula Y below:

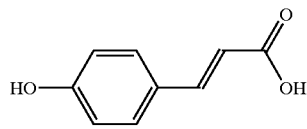

It is preferred that when the novel compound is Formula I and the aromatic moiety is benzylidene, the lipophilic moiety is not camphor.

Examples of hydrophilic moieties include nonionic groups such as polyoxyethylene chains having at least 2 ethylene oxide (EO) units, anionic groups such carboxylates, phosphates, sulfates, sulfonates, and cationic groups such as quaternary amines. A polyoxyethylene chain may have a degree of ethoxylation, i.e. number of ethylene oxide (EO) units, from 2 to about 150, preferably from 2 to about 100, more preferably from 2 to about 40 and most preferably from 2 to about 20. Again, as is known by those skilled in the art, the hydrophilic moiety may be selected and/or the degree of ethoxylation may be adjusted depending upon many factors, including the desired properties for the emulsifier and/or the desired properties an/or aesthetic appearance of the composition.

An example of a Formula I novel compound, based on a cinnamate aromatic moiety, a $C_{12}$ lipophilic moiety, and a polyethylene glycol hydrophilic moiety is depicted in Formula X below:

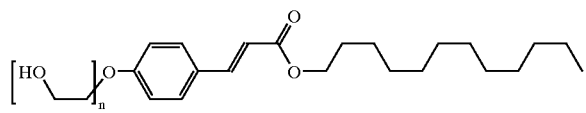

wherein n is preferably an integer from 2 to about 100.

The novel compound is present in the composition in an amount effective to provide a heterogeneous, stable emulsion. The novel compound is preferably present from about 0.01 to about 10 wt %, more preferably from about 0.1 to about 2 wt %, based upon the total weight of the composition.

Useful cosmetic, drug and medicinal actives include sunscreens, anti-aging agents, exfolients, anti-allergenics, anti-fungals, antimicrobials, anti-inflammatory agents, antipruritic agents, antiseptics, botanical extracts, de-pigmenting agents, pigmenting agents, anti-wrinkle agents, exfoliants, insect repellents, pharmaceutical agents, skin protectants, and vitamins. In the present composition, the cosmetic or medicinal active is a different compound or substance than the novel compound or the vehicle. Preferably, the actives used in the present invention have an aromatic moiety.

The aromatic moiety of the cosmetic, drug or medicinal active may be identical or nonidentical to the aromatic moiety of the novel compound. However, it is preferred that the aromatic moiety of the novel compound be substantially similar to, and more preferably identical to, the aromatic moiety of the cosmetic, drug or medicinal active.

An especially preferred embodiment of the present invention is a topical composition having a sunscreen active. Sunscreen actives especially useful in the present invention are those having one or more aromatic moieties. The aromatic moiety of the sunscreen active may be identical or nonidentical to the aromatic moiety of the novel compound. However, it is preferred that the aromatic moiety of the novel compound be substantially similar to, and more preferably identical to, the aromatic moiety of the sunscreen active.

For example, the novel compound having the methoxycinnamate moiety of Formula Y is preferably used in a composition that has a sunscreen active that is or includes octylmethoxycinnamate.

The sunscreen active(s) is preferably present at about 0.1 to 50 wt %, more preferably at about 1.0 wt % to about 35 wt %, and most preferably at about 5 wt % to about 25 wt %. As is known by those skilled in the art, the amount of sunscreen active can be adjusted depending on the level of sunscreen protection desired from the composition. Although not to be construed as limiting, it is preferable that the amount of sunscreen active employed provides a composition having an SPF range of about 2 to about 50, more preferably from about 15 to about 35, and most preferably from about 15 to about 30.

Useful sunscreen actives include those for UVA and UVB protection (290 to 400 nanometer solar radiation). Sunscreen actives having aromatic moieties for use with the present invention include, but are not limited to, oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, TEA salicylate, butylmethoxy dibenzoylmethane (avobenzone), 4-methyl benzilidene camphor, octyl triazone, 3-benzylidene camphor, benzylidene camphor sulfonic acid, terephthalydiene dicamphor sulfonic acid, ethyl PABA, hydroxy methylphenyl benzotriazole, diethylhexyl-2,6-naphthalate, di-T-butyl hydroxybenzylidene camphor, methylene bis-benzotriazoyltetramethylbutylphenol, bis-ethylhexyloxyphenol methoxyphenol triazine, or mixtures of the foregoing. Preferred sunscreen actives include oxybenzone, octyl methoxycinnamate and butylmethoxy dibenzoylmethane (avobenzone). It is also preferred that the sunscreen active, or combination of sunscreen actives, provides both UVA and UVB protection. Other useful sunscreen actives include those disclosed in U.S. Pat. No. 5,000,937, which is incorporated herein by reference in its entirety.

The present topical compositions, especially aqueous emulsions, have improved stability, dispersion and/or appearance. In addition, the novel compounds provide improved photostability of the sunscreen active (for example, avobenzone) and/or the composition.

The compositions may take the form of oil-in-water, water-in-oil emulsions, triple emulsions (e.g., o/w/o or w/o/w), or silicone emulsions (e.g., water-in-silicone or silicone-in-water). Oil-in-water emulsions are preferred. When the emulsion composition is aqueous, the composition preferably has about 10 wt % to about 90 wt % water, based on the total weight of the composition. More preferably, the composition has about 30 wt % to about 80 wt % water. Most preferably, the composition has about 50 wt % to about 70 wt % water.

The present composition can be made into any suitable product form. Such product forms include, but are not limited to, a gel, a cream, a lotion, an aerosol or pump spray, a stick, or incorporated into a patch or a towelette.

The novel compound can further be used as a solubilizer for cosmetic, drug or medicinal actives in single-phase, non-emulsion topical compositions such as a solution. The composition can have aqueous and/or organic vehicle content. The solubilizer takes on the same form, attributes, and advantages as disclosed herein for the novel compound.

The present composition may include any useful vehicle known in the art. Suitable vehicles and/or vehicle components include, but are not limited to, one or more vegetable oils; esters such as octyl palmitate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones and polysiloxanes; hydrocarbon oils such as mineral oil, petrolatum, isoeicosane and polyisobutene; polyols such as propylene glycol, glycerin, butylene glycol, pentylene glycol and hexylene glycol; or any mixtures of the foregoing.

The topical composition may also include conventional emulsifiers known in the art as useful in emulsifying or solubilizing cosmetic, drug or medicinal actives.

Optionally, the present composition may include one or more of the following additional ingredients: additional emulsifiers (e.g. anionic, cationic or nonionic), botanical extracts, chelating agents, colorants, emollients, film formers, fragrances, humectants, lubricants, moisturizers, preservatives, skin penetration enhancers, stabilizers, surfactants, thickeners, and viscosity modifiers.

Herein, all percentages are weight percentages based upon the total weight of the composition unless otherwise indicated.

The following are representative, nonlimiting examples of the present invention.

EXAMPLE 1

|  | Wt % |
| --- | --- |
| Water | QS to 100 |
| Glycerin | 1 to 10 |
| Carbomer 940 | 0.1 to 2 |
| Octyl methoxy cinnamate | 2 to 10 |
| Benzophenone-3 | 1 to 6 |
| Butylmethoxydibenzoyl methane | 1 to 3 |
| Emulsifiers of the L-A-H or A-L-H type (one or more) | 0.1 to 10 |
| Cetyl alcohol | 0.01 to 5 |
| Triethanolamine | 0.05 to 2 |
| Preservatives | 0.1 to 2 |

EXAMPLE 2

|  | Wt % |
| --- | --- |
| Water | QS to 100 |
| Tetrasodium EDTA | 0.2 |
| Veegum | 0.4 |
| Xanthan gum | 0.4 |
| Benzophenone-3 | 3.5 |
| Octylmethoxy cinnamate | 7.5 |
| Butylmethoxydibenzoyl methane | 3 |
| Merck IR 3535 | 10 |
| Emulsifier of the L-A-H or A-L-H type | 1.5 |
| DEA oleth-3 phosphate | 1.5 |
| Cyclomethicone | 5 |
| Methylparaben | 0.3 |
| Benzyl alcohol | 1 |
| Octyldodecanol | 4 |
| C12–15 Alkyl benzoate | 3 |
| Tocopheryl acetate | 0.2 |
| Cetyl alcohol | 0.5 |
| Dimethicone | 0.1 |
| Fragrance | 0.3 |

EXAMPLE 3

| Water | QS to 100 |
| --- | --- |
| Glycerin | 2.5 |
| Hydroxyethyl cellulose | 0.3 |
| Magnesium aluminum silicate | 0.3 |
| Disodium EDTA | 0.2 |
| Octyldodecyl neopentanoate | 3 |
| Glyceryl monostearate | 0.25 |
| Cetearyl alcohol | 1 |
| Emulsifier of the L-A-H or A-L-H type | 2 |
| Vitamin A palmitate | 0.1 |
| Octyl methoxy cinnamate | 7.5 |
| Octyl salicylate | 5 |
| Benzophenone-3 | 4 |
| Octocrylene | 5 |
| Butylmethoxydibenzoylmethane | 2 |
| Tricontanyl PVP | 3 |
| Benzyl alcohol | 1 |
| Methyl paraben | 0.3 |

EXAMPLE 4

| Water | qs to 100 |
| --- | --- |
| Emulsifier of the L-A-H or A-L-H type | 1.5 |
| Disodium EDTA | 0.2 |
| Xanthan gum | 0.35 |
| Magnesium aluminum silicate | 0.45 |
| Butylene glycol | 3 |
| C12–15 alkyl benzoate | 3 |
| Titanium dioxide | 3 |
| Octylmethoxy cinnamate | 7.5 |
| Benzophenone-3 | 3 |
| Methyl paraben | 0.3 |
| Imidazolidinyl urea | 0.3 |
| Cetyl alcohol | 1 |
| Glyceryl monostearate | 0.5 |
| Dimethicone | 1 |
| Hydrogenated polydecene | 1 |

EXAMPLE 5

| | |
|---|---|
| Water | QS to 100 |
| Glycolic Acid | 4 |
| Glycerin | 2.5 |
| Hydroxyethyl cellulose | 0.3 |
| Magnesium aluminum silicate | 0.3 |
| Disodium edta | 0.2 |
| Octyldodecyl neopentanoate | 5 |
| Glyceryl monostearate | 0.25 |
| Cetearyl alcohol | 2 |
| Emulsifiers of the L-A-H or A-L-H type | 2 |
| Vitamin A palmitate | 0.1 |
| Benzyl alcohol | 1 |
| Methyl paraben | 0.3 |
| Ammonium hydroxide (30% solution) | 1.8 |
| C12 to C15 alkyl benzoate | 3 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A topical composition, comprising:
   a cosmetic, drug or medicinal active;
   a compound having a formula selected from the group consisting of L—A—H and A—L—H, wherein L is a lipophilic moiety, wherein A is an aromatic moiety having an ultraviolet absorption maximum between 290 nanometers and 400 nanometers, and wherein H is a hydrophilic moiety; and
   a vehicle suitable for topical application, wherein when the compound is the formula L—A—H and the aromatic moiety is benzylidene, the lipophilic moiety is not camphor.

2. The composition of claim 1, wherein the active has an aromatic moiety.

3. The composition of claim 1, wherein the hydrophilic moiety is selected from the group consisting of a polyoxyethylene chain, a carboxylate, a phosphate, a sulfate, a sulfonate, and a quaternary amine.

4. The composition of claim 1, wherein the hydrophilic moiety is a polyoxyethylene chain having a degree of ethoxylation (n) of at least 2.

5. The composition of claim 4, wherein the polyoxyethylene chain has a degree of ethoxylation (n) from 2 to about 150.

6. The composition of claim 5, wherein the polyoxyethylene chain has a degree of ethoxylation (n) from 2 to about 40.

7. The composition of claim 6, wherein the polyoxyethylene chain has a degree of ethoxylation (n) from 2 to 20.

8. The composition of claim 1, wherein the lipophilic moiety is selected from the group consisting of a carbon chain of 2 to 24 carbon atoms, branched or unbranched, saturated or unsaturated, and a polyoxyalkylene chain of the formula (CxHyO)n, where x is 3 or more carbon atoms, n is 2 or more, and y is from 2x−2 to 2x.

9. The composition of claim 8, wherein the lipophilic moiety is a linear or branched alkyl group having from about 8 to about 18 carbon atoms.

10. The composition of claim 7, wherein the lipophilic moiety is a polyoxypropylene chain having a degree of propoxylation from 2 to about 160.

11. The composition of claim 10, wherein the polyoxypropylene chain has a degree of propoxylation from about 5 to about 40.

12. The composition of claim 11, wherein the polyoxypropylene chain has a degree of propoxylation from about 10 to about 20.

13. The composition of claim 1, wherein the aromatic moiety is selected from the group consisting of a salicylate, anthranilate, cinnamate, methoxycinnamate, ferulate, para amino benzoate, dibenzoyl methane, benzophenone, phenyl benzamidazole, cyano diphenyl acrylate, benzylidene, hydroxy benzylidene, biphenyl, terephthalylidene, triazine, naphthalene dicarboxylate, digallic acid, gallic acid, gallate, triazone, and any combinations thereof.

14. The composition of claim 1, wherein the aromatic moiety is selected from the group consisting of cinnamate, benzophenone, dibenzoylmethane, salicylate, and any combinations thereof.

15. The composition of claim 1, wherein the compound is present from about 0.01 wt % to about 10 wt % based on the total weight of the composition.

16. The composition of claim 1, wherein the compound is present from about 0.1 wt % to about 2 wt % based on the total weight of the composition.

17. The composition of claim 1, wherein the hydrophilic moiety is selected from the group consisting of a polyoxyethylene chain, carboxylate, phosphate, sulfate, sulfonate, and quaternary amine, wherein the lipophilic moiety is selected from the group consisting of a carbon chain of 2 to 24 carbon atoms, branched or unbranched, saturated or unsaturated, and a polyoxyalkylene chain of the formula (CxHyO)n, where x is 3 or more carbon atoms, n is 2 or more, and y is from 2x−2 to 2x, and wherein the aromatic moiety is selected from the group consisting of a salicylate, anthranilate, cinnamate, methoxycinnamate, ferulate, para amino benzoate, dibenzoyl methane, benzophenone, phenyl benzamidazole, cyano diphenyl acrylate, benzylidene, hydroxy benzylidene, biphenyl, terephthalylidene, triazine, naphthalene dicarboxylate, digallic acid, gallic acid, gallate, triazone, and any combinations thereof.

18. The composition of claim 1, wherein the composition is an emulsion, and wherein the compound is an emulsifying agent.

19. The composition of claim 18, wherein the emulsion is an oil-in-water emulsion.

20. The composition of claim 18, wherein the emulsion is a water-in-oil emulsion.

21. The composition of claim 1, wherein the active is a sunscreen active.

22. The composition of claim 21, wherein the compound is a photostabilizing agent.

23. The composition of claim 21, wherein the composition is an emulsion, and wherein the compound is a photostabilizing agent.

24. The composition of claim 20, wherein the cosmetic, drug or medicinal active is a sunscreen active.

25. The composition of claim 24, wherein said sunscreen active is selected from the group consisting of oxybenzone, sulisobenzone, dioxybenzone, menthyl anthranilate, para aminobenzoic acid, octyl methoxycinnamate, octocrylene, drometrizole trisiloxane, octyl salicylate, homomenthyl salicylate, octyl dimethyl PABA, TEA salicylate, butylmethoxy dibenzoylmethane, 4-methyl benzilidene camphor, octyl triazone, 3-benzylidene camphor, benzylidene camphor sulfonic acid, terephthalydiene dicamphor sulfonic acid, ethyl PABA, hydroxy methylphenyl benzotriazole, diethylhexyl-2,6-naphthalate, methylene bisbenzotriazoyltetra-methylbutylphenol, di-T-butylhydroxy benzilidene camphor, bis-ethylhexyloxyphenol methoxyphenol triazine, and any combinations thereof.

26. The composition of claim 24, wherein said sunscreen active is selected from the group consisting of oxybenzone, octyl methoxycinnamate, octyl salicylate, and butylmethoxydibenzoylmethane, and any combinations thereof.

27. The composition of claim 24, wherein the sunscreen active is present from about 0.1 wt % to about 50 wt % based on the total weight of the composition.

28. The composition of claim 24, wherein the sunscreen active is present from about 1 wt % to about 35 wt % based on the total weight of the composition.

29. The composition of claim 24, wherein the sunscreen active is present from about 5 wt % to about 25 wt % based on the total weight of the composition.

30. The composition of claim 24, wherein the aromatic moiety has a structure substantially similar to the sunscreen active.

31. The composition of claim 1, wherein the composition has a product form selected the group consisting of a gel, a cream, a lotion, an aerosol or pump spray, a stick, a patch and a towelette.

32. The composition of claim 1, wherein the cosmetic, drug or medicinal active is selected from the group consisting of sunscreen, anti-aging agent, exfollient, anti-allergenic, anti-fungal, antimicrobial, anti-inflammatory agent, anti-pruritic agent, antiseptic, anti-wrinkle agent, de-pigmenting agent, botanical extract, pigmenting agent, insect repellent, pharmaceutical agent, skin protectant, vitamin, and any combinations thereof.

33. The composition of claim 1, wherein the composition has an absorptivity value of about 5 or more.

34. A topical composition, comprising:
 a cosmetic, drug or medicinal active having an aromatic moiety;
 a compound having a formula selected from the group consisting of L—A—H and A—L—H, wherein L is a lipophilic moiety, wherein A is an aromatic moiety having an ultraviolet absorption maximum between 290 nanometers and 400 nanometers, and wherein H is a hydrophilic moiety; and
 a vehicle suitable for topical application, wherein the compound is present in an amount effective to provide at least one benefit selected from the group consisting of emulsifying the composition, photostabilizing the active, solubilizing the active, and any combinations thereof.

35. The composition of claim 34, wherein the composition has an absorptivity value of about 5 or more.

36. A method of improving the photostability of a composition comprising adding to the composition a compound having a formula selected from the group consisting of L—A—H and A—L—H, wherein L is a lipophilic moiety, wherein A is an aromatic moiety having an ultraviolet absorption maximum between 290 and 400 nanometers, wherein H is a hydrophilic moiety, and wherein when the compound is the formula L—A—H and the aromatic moiety is benzylidene, the lipophilic moiety is not camphor.

37. A method of improving the photostability of a composition having a sunscreen active comprising adding to the composition a compound having a formula selected from the group consisting of L—A—H and A—L—H, wherein L is a lipophilic moiety, wherein A is an aromatic moiety having an ultraviolet absorption maximum between 290 and 400 nanometers, wherein H is a hydrophilic moiety, and wherein when the compound is the formula L—A—H and the aromatic moiety is benzylidene, the lipophilic moiety is not camphor.

38. A method of improving the effectiveness of a sunscreen composition comprising adding to the composition a compound having a formula selected from the group consisting of L—A—H and A—L—H, wherein L is a lipophilic moiety, wherein A is an aromatic moiety having an ultraviolet absorption maximum between 290 and 400 nanometers, wherein H is a hydrophilic moiety, and wherein when the compound is the formula L—A—H and the aromatic moiety is benzylidene, the lipophilic moiety is not camphor.

39. A method of emulsifying a composition for topical application comprising adding to the composition a compound having a formula selected from the group consisting of L—A—H and A—L—H, wherein L is a lipophilic moiety, A is an aromatic moiety having a UV absorption maximum between 290 nanometers and 400 nanometers, and H is a hydrophilic moiety, and wherein the compound is present in an amount effective to form an emulsified composition.

40. The method of claim 36, wherein the hydrophilic moiety is a polyoxyethylene chain having a degree of ethoxylation (n) from 2 to about 40.

41. The method of claim 36, wherein the lipophilic moiety is selected from the group consisting of a carbon chain of 2 to 24 carbon atoms, branched or unbranched, saturated or unsaturated, and a polyoxyalkylene chain of the formula (CxHyO)n, where x is 3 or more n is 2 or more, and y is from 2x-2 to 2x.

42. The method of claim 36, wherein the lipophilic moiety is a polyoxypropylene chain having a degree of propoxylation from about 5 to about 40.

43. The method of claim 36, wherein the aromatic moiety is selected from the group consisting of a cinnamate, benzophenone, dibenzoylmethane, salicylate, and any combinations thereof.

44. The method of claim 36, wherein the compound is present from about 0.01 wt% to about 10 wt% based on the total weight of the composition.

45. The method of claim 36, wherein the hydrophilic moiety is selected from the group consisting of a polyoxyethylene chain, carboxylate, phosphate, sulfate, sulfonate, and quaternary amine, wherein the lipophilic moiety is selected from the group consisting of a carbon chain of 2 to 24 carbon atoms, branched or unbranched, saturated or unsaturated, and a polyoxyalkylene chain of the formula (CxHyO)n, wherein x is 3 or more carbon atoms, n is 2 or more, and y is from 2x-2 to 2x, and wherein the aromatic moiety is selected from the group consisting of a salicylate, anthranilate, cinnamate, methoxycinnamate, furulate, para amino benzoate, dibenxoyl methane, benzophenone, phenyl benzamidazole, cyano diphenyl acrylate, benzylidene, hydroxy benzylidene, biphenyl, terephthalylidene, triazine, naphthalene dicarboxylate, digallic acid, gallic acid, gallate, triazone, and any combinations thereof.

46. The method of claim 37, wherein the hydrophilic moiety is a polyoxyethylene chain having a degree of ethoxylation (n) from 2 to about 40.

47. The method of claim 37, wherein the lipophilic moiety is selected from the group consisting of a carbon chain of 2 to 24 carbon atoms, branched or unbranched, saturated or unsaturated, and a polyoxyalkylene chain of the formula (CxHyO)n, where x is 3 or more carbon atoms, n is 2 or more, and y is from 2x-2 to 2x.

48. The method of claim 37, wherein the lipophilic moiety is a polyoxypropylene chain having a degree of propoxylation from about 5 to about 40.

49. The method of claim 37, wherein the aromatic moiety is selected from the group consisting of a cinnamate, benzophenone, dibenzoylmethane, salicylate, and any combinations thereof.

50. The method of claim 37, wherein the compound is present from about 0.01 wt % to about 10 wt % based on the total weight of the composition.

51. The method of claim 37, wherein the hydrophilic moiety is selected from the group consisting of a polyoxyethylene chain, carboxylate, phosphate, sulfate, sulfonate, and quaternary amine, wherein the lipophilic moiety is selected from the group consisting of a carbon of 2 to 24 carbon atoms, branched or unbranched, saturated or unsaturated, and a polyoxylkylene chain of the formula (CxHyO)n, where x is 3 or more carbon atoms, n is 2 or more, and y is from 2x-2 to 2x, and wherein the aromatic moiety is selected from the group consisting of a salicylate, anthranilate, cinnamate, methoxycinnamate, ferulate, para amino benzoate, dibenzoyl methane, benzophenone, phenyl benzamidazole, cyano diphenyl acrylate, benzophene, hydroxy benzylidene, biphenyl, terephthalyidene, triazine, naphthalene dicarboxylate, digallic acid, gallic acid, gallate, triazone, and any combinations thereof.

52. The method of claim 38, wherein the hydrophilic moiety is a polyoxyethylene chain having a degree of ethoxylation (n) from 2 to about 40.

53. The method of claim 38, wherein the lipophilic moiety is selected from the group consisting of a carbon chain of 2 to 24 carbon atoms, and a polyoxyalkylene chain of the formula (CxHyO)n, where x is 3 or more carbon atoms, n is 2 or more, and y is from 2x-2 to 2x.

54. The method of claim 38, wherein the lipophilic moiety is a polyoxypropylene chain having a degree of propoxylation from about 5 to about 40.

55. The method of claim 38, wherein the aromatic moiety is selected from the group consisting of a cinnamate, benzophenone, dibenzoulmethane, salicylate, and any combinations thereof.

56. The method of claim 38, wherein the compound is present from about 0.01 wt % to about 10 wt % based on the total weight of the composition.

57. The method of claim 38, wherein the hydrophilic moiety is selected from the group consisting of a polyoxyethylene chain, carboxylate, phosphate, sulfate, sulfonate, and quaternary amine, consisting of a carbon chain of 2 to 24 carbon atoms, branched or unbranched, saturated or unsaturated, and a polyoxyalkylene chain of the formula (CxHyO)n, where x is 3 or more carbon atoms, n is 2 or more, and y is from 2x-2 to 2x, and wherein the aromatic moiety is selected from the group consisting of a salicylate, anthranilate, cinnamate, methoxycinnamate, ferulate, para amino benzoate, dibenzoyl methane, benzophenone, phenyl benzamidazole, cyano diphenyl acrylate, benzylidene, hydroxy benzylidene, biphenyl, terephthalylidene, triazine, naphthalene dicarboxylate, digallic acid, gallic acid, gallate, triazone, and any combinations thereof.

58. The method of claim 39, wherein the hydrophilic moiety is a polyoxyethylene chain having a degree of ethoxylation (n) from 2 to about 40.

59. The method of claim 39, wherein the lipophilic moitey is selected from the group consisting of a carbon chain of 2 to 24 carbon atoms, branched or unbranched, saturated or unsaturated, and a polyoxyalkylene chain of the formula, (CxHyO)n, where x is 3 or more carbon atoms, n is 2 or more, and y is from 2x-2 to 2x.

60. The method of claim 39, wherein the lipophilic moiety is a polyoxypropylene chain having a degree of propoxylation from about 5 to about 40.

61. The method of claim 39 wherein the aromatic moiety is selected from the group consisting of a cinnamate, benzophenone, dibenzoylethane, salicylate, and any combinations thereof.

62. The method of claim 39, wherein the second compound is present from about 0.01 wt % to about 10 wt % based on the total weight of the composition.

63. The method of claim 39, wherein the hydrophilic moiety is selected from the group consisting of a polyoxyethylene chain, carboxylate, phoshate, sulfate, sulfonate, and quaternary amine, consisting of a carbon chain of 2 to 24 carbon atoms, branched or unbranched, saturated or unsaturated, and a polyoxyalkylene chain of the formula (CxHyO)n, where x is 3 or more carbon atoms, n is 2 or more, and y is from 2x-2 to 2x, and wherein the aromatic moiety is selected from the group consisting of a salicylate, anthranilate, cinnamate, methoxycinnamate, ferulate, para amino benzoate, dibenzoyl methane, benzophenone, phenyl benzamidazole, cyano diphenyl acrylate, benzylidene, hydroxy benzylidene, biphenyl, terephthalylidene, triazine, naphthalene dicarboxylate, digallic acid, gallic acid, gallate, triazone, and any combinations thereof.

* * * * *